United States Patent [19]

Skrhak

[11] Plant 5,147

[45] Nov. 29, 1983

[54] PEACH TREE "PEPPERMINT"

[76] Inventor: Sam S. Skrhak, Rte. 2, Box 116P, McGregor, Tex. 76657

[21] Appl. No.: 392,957

[22] Filed: Jun. 28, 1982

[51] Int. Cl.[3] ..... A01H 5/03

[52] U.S. Cl. ..... Plt./43

[58] Field of Search ..... Plt./43

*Primary Examiner*—Robert E. Bagwill

[57] ABSTRACT

Disclosed herein is a new and distinct variety of peach tree which is particularly distinguished by its large and unique rose red flecked and streaked doubled flowers.

5 Drawing Figures

ORIGIN

This new and distinct variety of peach tree was discovered among seedlings being grown for grafting rootstock at the edge of my garden. I had planted seeds from my own orchard and from various sources so the parentage of this particular tree is unknown. It was first observed blooming in March 1977. It was first asexually reproduced in February 1979 by grafting in my orchard, located near McGregor, Tex. and showed that its characteristics come true to form in every respect and transmitted through succeeding generations. In June 1981 bud stock was sent to the Texas A and M University Horticulture Department at College Station, Tex. for further evaluation.

SUMMARY

This variety of peach tree is medium size, vigorous, and upright spreading. It is distinguished from all other peach varieties by being an abundant producer of uniquely marked doubled flowers. Each flower being individually marked, they range from an entire flower being near white-pinkish to a completely rose pink with various combinations of flecks and streaks between these two extremes.

PHOTOGRAPHS

The accompanying photographs show typical specimens of flowers of my new variety as depicted in color as nearly true as possible in an illustration of this type.

DESCRIPTION

The following is a detailed description of the new variety of peach tree, its foliage and its flowers based upon observation of specimens grown near McGregor, Tex. with color terminology referenced to Reinhold Color Atlas by A. Kornerup and J. H. Wanscher:

Tree:
- *Size.*—Medium.

- *Vigor.*—Vigorous.
- *Form.*—Upright spreading.
- *Density.*—Medium dense.

Branches:
- *Size.*—Medium.
- *Lenticels.*—Medium size and number.
- *Internodes.*—Average $\frac{3}{4}''$ long.

Leaves:
- *Size.*—Medium-average length $5\frac{1}{2}''$, average width $1\frac{1}{4}''$.
- *Form.*—Lanceolate, acutely pointed.
- *Color.*—Upper surface — Dark green (28F7). Lower surface — Grayish green (28E5 to 28E6).
- *Petiole.*—Medium length and thickness.
- *Glands.13* Average number 2; opposite; medium size; reniform; positioned on upper part of petiole.

Flower buds:
- *Size.*—Large.
- *Length.*—Long.

Flowers:
- *Date of first blossoms.*—Relatively early; first week of March; about one week earlier than Melba Peach.
- *Overall appearance.*—Very showy.
- *Size.*—Large, average $1\frac{3}{4}''$.
- *Petalage.*—15 to 25 petals.
- *Color.*—Petal near white to pinkish white (lighter than 12A2); flecked and streaked with rose red (12B8).

The tree and its flowers herein described may vary somewhat depending on its growing environment. The description is that of a specimen grown near McGregor, Tex.

I claim:

1. A new and distinct variety of peach tree substantially as herein described and illustrated, characterized particularly by its bearing of large uniquely colored double flowers.

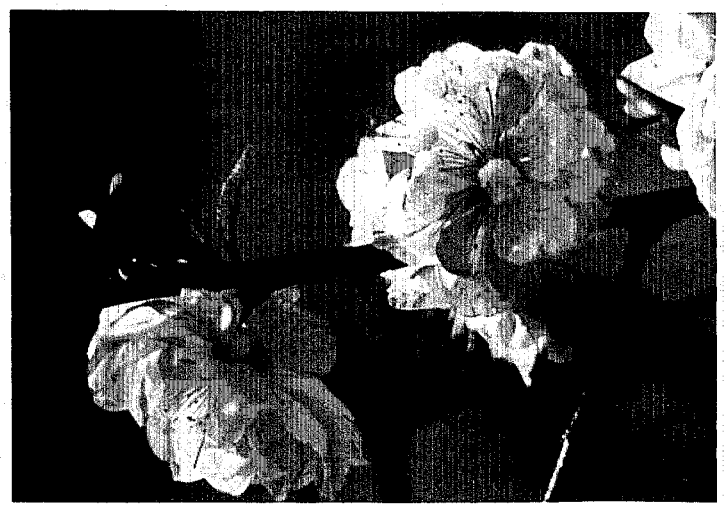
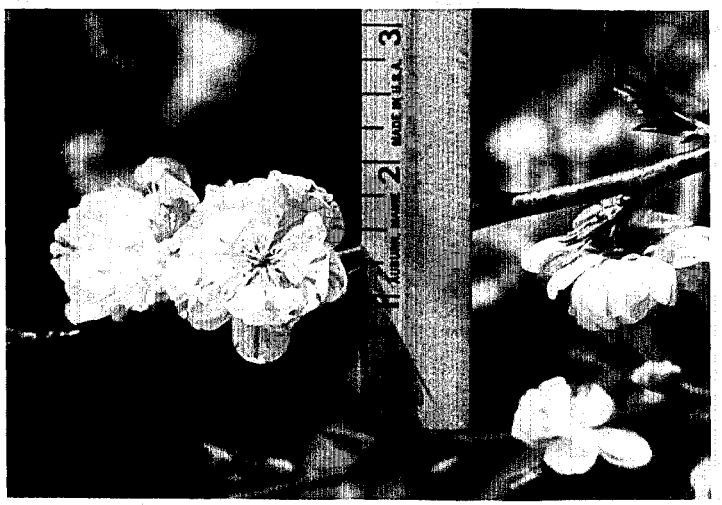
1
2
3
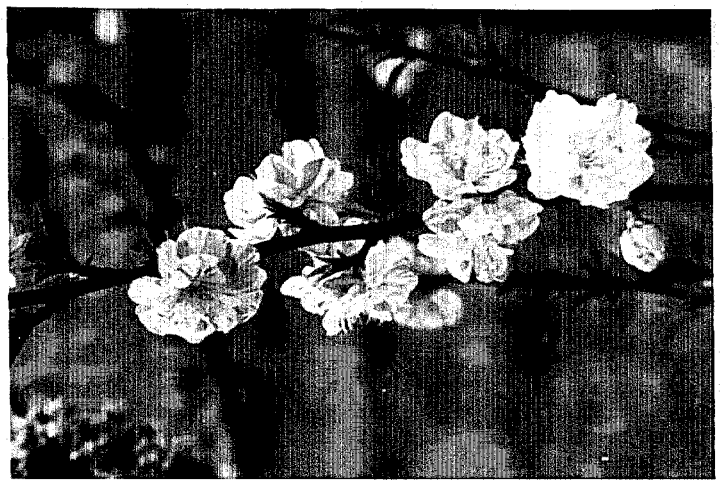

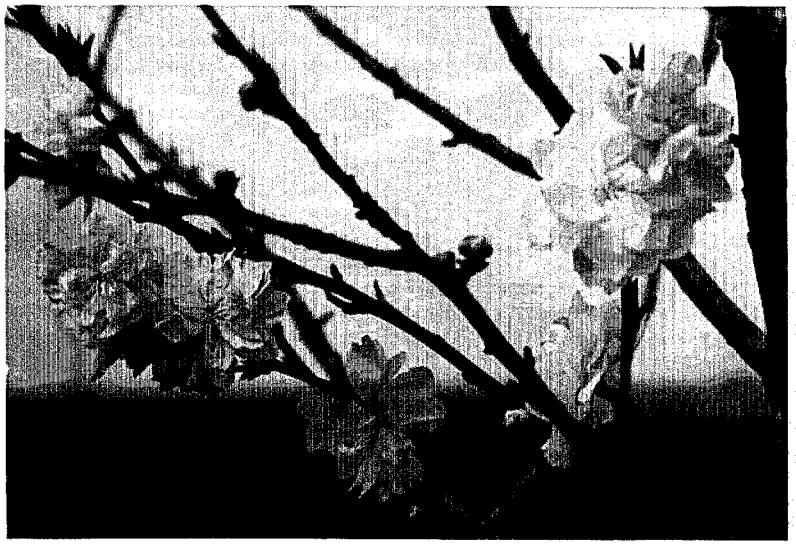
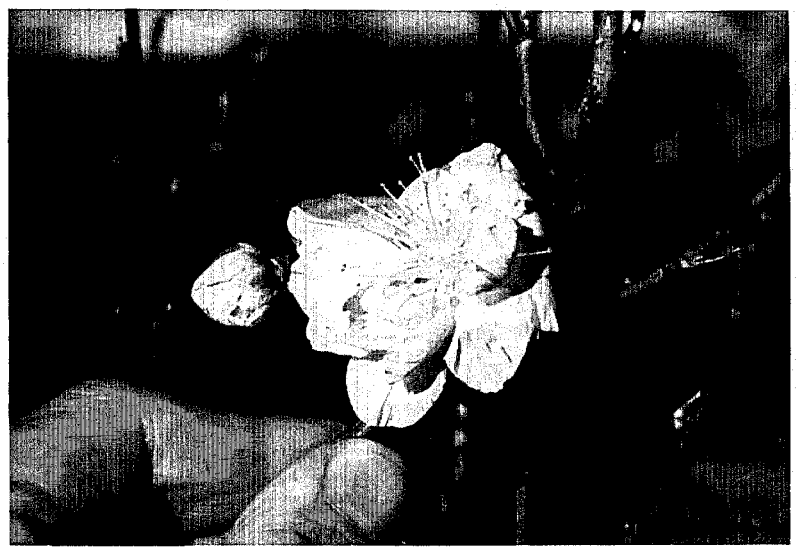

* * * * *